(12) United States Patent
McLachlin et al.

(10) Patent No.: US 10,441,365 B2
(45) Date of Patent: Oct. 15, 2019

(54) PATIENT REFERENCE DEVICE

(71) Applicants: Stewart David McLachlin, Toronto (CA); Gal Sela, Toronto (CA); Kamyar Abhari, Toronto (CA); Kai Michael Hynna, Toronto (CA); Jared Rowland Shoup, Olive Branch, MS (US); Aidan Alan Thompson, Thornhill (CA)

(72) Inventors: Stewart David McLachlin, Toronto (CA); Gal Sela, Toronto (CA); Kamyar Abhari, Toronto (CA); Kai Michael Hynna, Toronto (CA); Jared Rowland Shoup, Olive Branch, MS (US); Aidan Alan Thompson, Thornhill (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 465 days.

(21) Appl. No.: 15/403,629

(22) Filed: Jan. 11, 2017

(65) Prior Publication Data

US 2018/0193097 A1  Jul. 12, 2018

(51) Int. Cl.
*A61B 34/20* (2016.01)
*A61B 34/00* (2016.01)
(Continued)

(52) U.S. Cl.
CPC ..... *A61B 34/20* (2016.02); *A61B 2017/00119* (2013.01); *A61B 2017/00221* (2013.01);
(Continued)

(58) Field of Classification Search
None
See application file for complete search history.

(56) References Cited

U.S. PATENT DOCUMENTS 8,945,130 B2 * 2/2015 Tuma ................ A61B 17/1668
606/79
9,414,859 B2 * 8/2016 Ballard ............. A61B 17/7002
(Continued)

FOREIGN PATENT DOCUMENTS

CA          2958013 A1    4/2017
WO       2004049109       6/2004
(Continued)

OTHER PUBLICATIONS

UKIPO, UK Search Report relating to UK application No. 1800352.5, dated Jun. 21, 2018.
(Continued)

*Primary Examiner* — Brian T Gedeon
(74) *Attorney, Agent, or Firm* — Rowand LLP

(57) ABSTRACT

Methods and devices to track patient anatomy during a surgical operation. A patient reference device is attached to an anatomical feature of a patient and it includes an attachment base and an optically-trackable array detectable by an optical navigation system and having a longitudinally-extending arm to space apart the fixed geometric pattern from the anatomical feature. The arm includes a connector to be detachably secured to the attachment base. An inertial measurement unit within the attachment base enables determining, based on comparing a threshold level to a motion signal, that the attachment base has changed position, wherein the motion signal represents the change in position and its magnitude. Based on determining that the attachment base has changed position an alarm signal is generated an and an output device in the attachment base outputs an alarm in response to the alarm signal.

20 Claims, 7 Drawing Sheets

(51) Int. Cl.
    *A61B 90/00* (2016.01)
    *A61B 17/00* (2006.01)
(52) U.S. Cl.
    CPC .............. *A61B 2017/00477* (2013.01); *A61B 2017/00734* (2013.01); *A61B 2017/00876* (2013.01); *A61B 2034/2048* (2016.02); *A61B 2034/2055* (2016.02); *A61B 2090/037* (2016.02); *A61B 2090/3937* (2016.02); *A61B 2090/3983* (2016.02); *A61B 2090/3991* (2016.02)

(56) References Cited

U.S. PATENT DOCUMENTS

| | | | |
|---|---|---|---|
| 10,144,637 B2* | 12/2018 | Bai | H04W 4/029 |
| 2010/0249581 A1* | 9/2010 | McCombs | A61B 90/36 600/426 |
| 2011/0263971 A1* | 10/2011 | Nikou | A61B 90/39 600/424 |
| 2015/0313684 A1 | 11/2015 | Fanson et al. | |
| 2016/0113783 A1 | 4/2016 | Hladio et al. | |
| 2016/0262913 A1* | 9/2016 | Kling | A61F 5/01 |
| 2016/0361101 A1 | 12/2016 | Moctezuma de la Barrera et al. | |
| 2017/0007353 A1* | 1/2017 | Fleig | A61B 90/39 |
| 2017/0119475 A1* | 5/2017 | McCabe | A61B 34/20 |
| 2018/0045512 A1* | 2/2018 | Uhde | A61B 90/39 |
| 2018/0064496 A1* | 3/2018 | Hladio | A61B 46/10 |
| 2018/0071029 A1* | 3/2018 | Srimohanarajah | A61B 46/10 |
| 2018/0303558 A1* | 10/2018 | Thomas | A61B 34/10 |
| 2019/0053852 A1* | 2/2019 | Schoenefeld | A61B 17/15 |

FOREIGN PATENT DOCUMENTS

| | | |
|---|---|---|
| WO | 2017064254 A1 | 4/2017 |
| WO | 2017151734 A1 | 9/2017 |

OTHER PUBLICATIONS

Canadian Intellectual Property Office, Examiner's Report dated Sep. 13, 2017 relating to application No. 2,958,013.
Zimmer: "iAssist Knee Surgical Technique" dated Jul. 13, 2015, retrieved from http://www.zimmer.com/content/dam/zimmer-web/documents/en-US/pdf/surgical-techniques/knee/iassist-knee-surgical-technique.pdf.
Apple Inc.'s MagSafe laptop power cord connector.

* cited by examiner

PATIENT REFERENCE DEVICE

FIELD

The present application generally relates to optical navigation systems used in surgical operations and, in particular, to a patient reference device to be attached to the patient and tracked by an optical navigation system.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimens, and radiation therapy are only a few examples of procedures utilizing imaging guidance in the medical field. Optical tracking systems, used during a medical procedure, track the position of a part of the instrument that is within line-of-site of the optical tracking camera. These optical tracking systems also require a reference to the patient to know where the instrument is relative to the target (e.g., a tumour) of the medical procedure, or to accurately assess positioning of relative parts of patient anatomy or orthopedic medical devices.

In some surgeries, a patient reference device that includes an optically-trackable component that the navigation system is capable of tracking is fixedly attached to the patient. Provided a proper registration process in undertaken, the navigation system is then able to determine the position of patient anatomy in its coordinate space, so that it is able to track (and display) patient anatomy relative to tracked instruments and devices by also tracking the patient reference device.

In some cases, the patient reference device may be inadvertently bumped during the surgery which can move the patient reference device, cause it to break, or cause the bone to which it is attached to fracture. If the device moves relative to the patient, then the registration is lost and the surgery must either proceed without navigation or it must be stopped to reattach the device and re-perform the registration process. At worst the movement of the patient reference device is not noticed and the surgery proceeds using an inaccurate registration. Accordingly, it would be advantageous to reduce the likelihood of loss of registration and to accurately determine whether re-registration is necessary.

BRIEF SUMMARY

The present application describes a patient reference device for tracking anatomical location of a patient by an optical navigation system during a surgical procedure. The patient reference device includes an attachment base having an attachment mechanism to secure the attachment base to an anatomical feature of the patient; a optically-trackable array including a plurality of fiducials in a fixed geometric pattern to be detected by the optical navigation system and having a longitudinally-extending arm to space apart the fixed geometric pattern from the anatomical feature, the arm including a connector to be detachably secured to the attachment base; an inertial measurement unit in the attachment base to detect a change in position of the attachment base and to output a motion signal representing the change in position and its magnitude; a logic circuit to receive the motion signal and to compare it to a threshold level and, if the motion signal exceeds the threshold level, to generate an alarm signal; and an output device to output an alarm in response to the alarm signal.

In another aspect, the present application describes a method of tracking patient anatomy during a surgical operation using an optical navigation system and a patient reference device, the patient reference device being attached to an anatomical feature of the patient, the patient reference device including an attachment base having an attachment mechanism to secure the attachment base to the anatomical feature and a optically-trackable array including a plurality of fiducials in a fixed geometric pattern to be detected by the optical navigation system and having a longitudinally-extending arm to space apart the fixed geometric pattern from the anatomical feature, the arm including a connector to be detachably secured to the attachment base. The method includes determining, based on comparing a threshold level to a motion signal from an inertial measurement unit within the attachment base, that the attachment base has changed position, wherein the motion signal represents the change in position and its magnitude; based on determining that the attachment base has changed position, generating an alarm signal; and outputting, via an output device in the attachment base, an alarm in response to the alarm signal.

In yet a further aspect, the present application describes non-transitory computer-readable media storing computer-executable program instructions which, when executed, configured a processor and/or logic circuitry to perform the described methods.

Other aspects and features of the present application will be understood by those of ordinary skill in the art from a review of the following description of examples in conjunction with the accompanying figures.

In the present application, the term "and/or" is intended to cover all possible combination and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

BRIEF DESCRIPTION OF THE DRAWINGS

Reference will now be made, by way of example, to the accompanying drawings which show example embodiments of the present application, and in which.

DESCRIPTION OF EXAMPLE EMBODIMENTS

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principles available with each modality. CT is often used to visualize bony structures and blood vessels when used in conjunction with an intra-venous agent such as an iodinated contrast agent. MRI may also be performed using a similar contrast agent, such as an intra-venous gadolinium-based contrast agent which has pharmaco-kinetic properties that enable visualization of tumors and break-down of the blood brain barrier. These multi-modality solutions can provide varying degrees of contrast between different tissue types, tissue function, and disease states. Imaging modalities can be used in isolation, or in combination to better differentiate and diagnose disease.

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimens, and radiation therapy are only a few examples of procedures utilizing imaging guidance in the medical field. Optical tracking systems, used during a medical procedure, track the position of a part of the instrument that is within line-of-site of the optical tracking camera.

Figure 1:
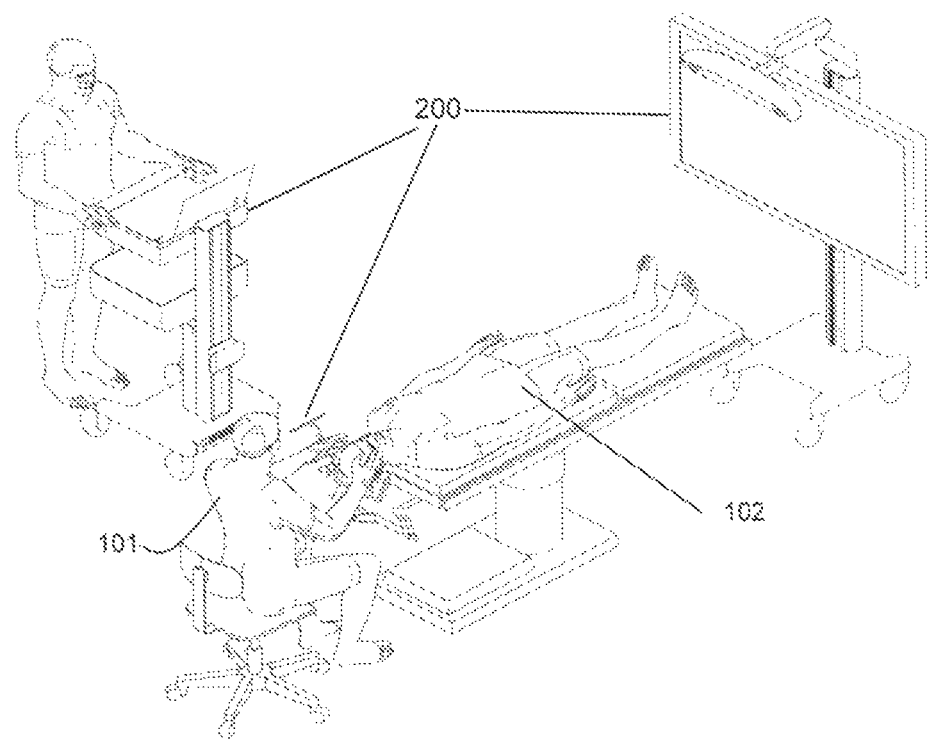
FIG. 1 diagrammatically illustrates, in perspective view, a navigation system.

In surgical operations in particular, optical tracking is useful for displaying a live real-time image that combines pre-operative scan data with instrument location. This can assist, for example, a neurosurgeon in guiding an instrument to a treatment location within the brain. An example of an image-guided surgical suite is shown in FIG. 1, which diagrammatically illustrates, in perspective view, a navigation system 200, such as a medical navigation system. The navigation system 200 is positioned in an operating room ("OR") to be used to guide a surgeon in conducting a surgical procedure. In this example, the navigation system 200 supports, facilitates, and enhances minimally-invasive access port based surgery using a minimally-invasive access port-based surgical procedure. In this example, a surgeon 101 conducts a minimally-invasive access port based surgery on a subject, such as a patient 102, in an OR environment. The surgery may be a neurosurgery, as in this example. In these circumstances, the surgeon 101 is positioned proximate the head of the patient 102.

In addition to the navigation system 200, the operating room may contain other equipment, such as surgical tool trays, carts, and booms. Some of this equipment may feature surgical lights, oxygen or other gas supplies, anesthesia supplies, etc., depending on the nature of the surgery being performed.

Figure 2:
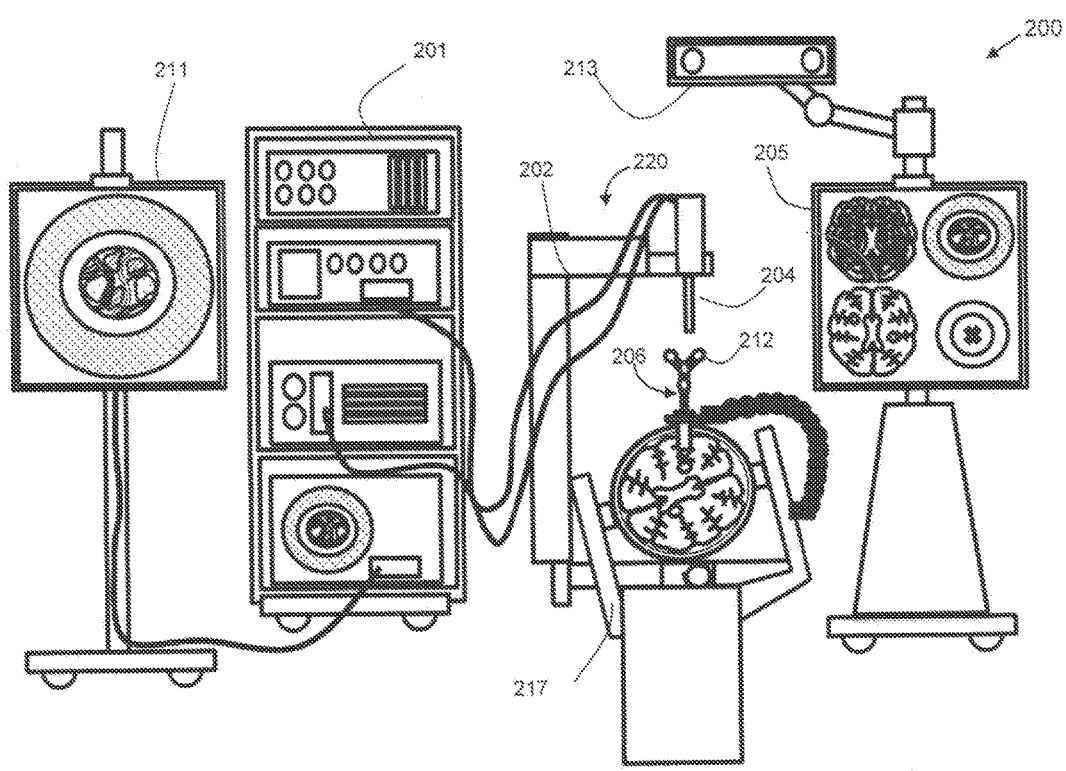
FIG. 2 shows, in block diagram form, an example of the navigation system.

Reference is now made to FIG. 2, which diagrammatically illustrates an example of the navigation system 200. The navigation system 200 may include an equipment tower 201, a tracking system 213, and at least one display device. e.g., a primary display device 211 and a secondary display device 205. The tracking system 213 may include optical imaging devices, e.g. cameras. In this example, the tracking system 213 includes two laterally spaced-apart cameras for stereoscopic vision. The camera may be a three-dimensional (3D) optical tracking stereo camera, such as a Northern Digital Imaging® (NDI) optical tracking stereo camera, by way of example. The navigation system 200 may be used to track at least one instrument, such as a surgical instrument, e.g., an access port 206, for assisting the surgeon 101 during the surgical procedure.

In some embodiments, the navigation system 200 may further include a device positioning unit, also referred to as a drive unit 220, having a robotic arm 202 that supports an optical device, such as an optical scope 204 or camera. In the case where the optical scope 204 includes an image sensor, like a camera, the view may be displayed on one of the displays 205, 211 to assist the surgeon 101 in navigation. The view may also be integrated with other data, including pre-surgical plan information, pre-surgical imaging (like MRI, CAT scan, or ultrasound imaging, for example), and may be registered on the basis of registration of the patient in the OR space and registration of the surgical equipment relative to the patient, as tracked by the navigation system 200. The navigation system 200 may also track surgical instruments, like the access port 206 or other tools, in the OR space and may map models of those tools to a virtual space to which patient data has been mapped in order to render a combined display of the tools and the patient and/or pre-surgical imaging on the displays 205, 211.

The equipment tower 201 may be mountable on a frame, e.g., a rack or a cart, and is configured to accommodate at least one of a computer operable by at least one a set of instructions, storable in relation to at least one non-transitory memory device, corresponding to at least one of planning software, navigation software, and robotic software, and a power supply, e.g., an AC adapter power supply.

In some example surgeries, a patient's head may be retained by a head holder 217, a craniotomy is performed, a dura flap is formed and retracted, and the access port 206 is inserted into the patient's brain. The tracking system 213 tracks and determines, e.g., in real-time by way of a set of instructions corresponding to tracking software and storable in relation to at least one non-transitory memory device, location data of at least one OR item, such as the robotic arm 202 and the at least one instrument, e.g., the access port 206. The tracked instrument may include at least one fiducial marker 212 mounted in fixed relation to the at least one OR item, e.g., the robotic arm 202 and the at least one instrument, e.g., the access port 206.

The secondary display device 205 may be configured to display real-time output from the navigation system 200. The displayed data may include at least one of an axial view, a sagittal view, at least one coronal view, and a view oriented relative to the at least one instrument, such as perpendicular to a tool tip, in-plane of a tool shaft, etc. The display may include multiple views.

The fiducial marker 212 may be a reflective sphere where the tracking system 213 is an optical tracking device. In some embodiments, the tracking system 213 may detect electromagnetic emissions and the fiducial marker 212 may be an electromagnetic marker. The three-dimensional position of the at least one fiducial marker 212 is determined by the tracking system 213 which is then able to map the location of the fiducial marker 212 to a virtual coordinate space and, thereby, position a model of the instrument to which the fiducial marker 212 is attached in the virtual coordinate space. The marker positions could be tracked relative to an object in the operating room such as the patient. Other types of markers that could be used would be radio frequency ("RF"), electro-magnetic ("EM"), light emitting diodes ("LED") (pulsed and un-pulsed), glass spheres, reflective stickers, or unique structures and patterns. The RF and EM may have specific signatures for the specific tools to which they are attached. The reflective stickers, structures, and patterns, glass spheres, LEDs may be detected using optical detectors, while RF and EM may be detected by using antennas.

In the case of surgical navigation systems, registration is also important to ensure that the location of the patient is determined in terms of its position in the coordinate system. Then the system is accurately able to track the location of objects relative to the patient. That registration process, in various implementations, can be performed in relation to a base reference frame and is performable by various techniques, such as (a) identifying features (natural or engineered) on the MRI and CT images and pointing to those same features in the live scene using a pointer tool that is tracked by the tracking system; (b) tracing a line on the curved profile of the patient's anatomy with a pointer tool that is tracked by the tracking system and matching this curved profile to the 3D MRI or CT volume; (c) applying a tool of known geometry to the patient's anatomy, where the tool is trackable by the tracking system; and (d) using a surface acquisition tool based on structured light or a 3D scanner and matching an extracted surface to the 3D MRI or CT volume. As an example, registration using fiducial touch-points may include first identifying fiducial touch-points on images, then touching the fiducial touch-points with a tracked instrument and determining registration data in relation to reference markers. In another example, the registration may involve conducting a surface scan procedure by scanning the patient's anatomy using a 3D scanner, extracting the surface data from MRI/CT data, and determining registration data points by matching the surface data from the 3D scanner with the surface data from MRI/CT data. These techniques may be used in tandem to complete a registration. In some procedures, an initial registration may be supplemented or refined with additional registration operations during the course of a surgery.

Registration typically includes identifying the location of the patient anatomy relative to an optically-tracked patient reference device or marker that can be tracked by the navigation system and which is in a fixed position relative to the patient anatomy of interest. Generally, this may be accomplished by attaching the patient reference device to a patient immobilization frame (such as a clamp for skull fixation in neurosurgery), which itself is rigidly attached to the patient. The patient reference device is typically a unique optical array, such as a fixed geometric pattern or arrangement of fiducials, that serves as a reference point for the navigation system. The registration process links the optically-detected location of the patient reference device to the optically-detected location of various landmarks or known points on the patient using one or more of the techniques described above by determining the three-dimensional location of both in the navigation coordinate system.

After registration, the patient reference device is used by the optical navigation system to pinpoint the location of the patient in the coordinate system so that it can track the position of trackable objects relative to the patient.

Because the patient reference device is typically a physical structure protruding outwards and in close proximity to the patient, there is a risk that the patient reference device may be bumped or dislodged during the surgical operation. If this occurs, the surgical operation may need to be stopped to redo the registration process. Alternatively, the surgical operation may be continued without relying on the navigation system any further. In some cases, the misalignment may be slight enough not to be noticed by persons in the operating room and the procedure might inadvertently be carried out in reliance on the navigation system which has now lost registration with the actual anatomical location of the patient. The phrase "lost registration", in many embodiments, may refer to a reduction in the accuracy of the registration below a defined threshold minimum accuracy.

Some types of surgeries do not include an equivalent to the head clamp that immobilizes the patient's cranium during neurosurgery. For example, in some orthopedic surgeries, the patient may be only partly immobilized and portions of the patient anatomy may be expected to be manipulable during the surgery. In some such cases, the patient reference device may be directly attached to the patient anatomy. For example in some cases the patient reference device may be attached to bone using a drill and screws to secure the patient reference device in place relative to the patient anatomy.

Screw-based attachment may not be suitable for some surgeries, such as, for example some spinal surgeries. In some such cases, attachment of the patient reference device to patient anatomy is by way of another attachment mechanism, such as a mechanical clamp with jaws that can be secured to a bony structure, adhesive (to bone or skin), or a pin or other penetrating device. In some spinal surgeries, the patient reference device might be intended to be attached to certain vertebrae that are expected to stay (more or less) stationary during the surgery. In some cases, the attachment is to the lumbar vertebrae.

It will be appreciated that if the attachment mechanism is a clamp, adhesive or other such attachment mechanism, as opposed to screws/bolts, then there is a chance that bumping of the patient reference device may more easily dislodge or at least shift the position of the attachment mechanism, even where the patient reference device itself is not bent or broken. This becomes that much more difficult to identify in the case of a surgical operation in which the patient anatomy is not fully immobilized. It may be unclear whether the patient has moved or whether the patient reference device has moved relative to the patient. The latter would necessitate re-attachment and re-registration.

The present application describes a multi-piece patient reference device having an attachment base to be detachably secured to patient anatomical feature and an optically-trackable array that is detachably secured to the attachment base. In some cases, the optically-trackable array may be attached using a quick-break attachment that allows the array to be knocked off relatively easily if bumped so as to ensure that no bumping forces are transferred to the attachment base. This helps avoid bumping and dislodgement or disturbance of the attachment base relative to the anatomy, so that the optically-trackable array may be easily reattached, via the quick-break attachment, without necessitating a re-registration. In some cases, the quick-break attachment is a magnetic coupling between the attachment base and the optically-trackable array. The attachment base may feature a relatively low profile to ensure that it is unlikely to be bumped accidentally.

In some embodiments, the attachment base may include an inertial measurement unit ("IMU") to detect movement of the attachment base. In some implementations the inertial measurement unit includes one or more accelerometers and gyroscopes. In some embodiments, the IMU includes one or more magnetometers, which help with correcting for orientation drift. A typical example IMU may include three accelerometers arranged orthogonally to each other for measuring inertial acceleration, and three gyroscopes arranged orthogonally to each other to measure rotational position. References herein to an IMU include an Attitude and Heading Reference System (AHRS), which typically includes an IMU and some on-board processing. The IMU, together with a logic circuit for detecting more than a threshold change in IMU measurements, may allow for determination of whether the attachment base has moved. The attachment base may include an output device that may signal, perhaps visually or audibly, when the attachment base has moved. In this manner, if the optically-trackable array is bumped and detached from the attachment base, before reattaching it and relying on it without requiring re-registration, the surgeon or other operating room personnel can confirm that the attachment base has not moved.

It will be appreciated that the attachment base may move relative to the patient anatomy or the patient anatomy may move causing movement of the attachment base. In some embodiments, this movement is indistinguishable to the attachment base. In fact, during a surgical procedure the patient anatomy may be intentionally moved. In that case, the IMU may be "reset" so as to treat the newly-moved stationary position of the anatomy as the "zero" location from which future movement will be detected.

In some cases, the output device may include a visual output, such as an LED for example, an auditory output, such as a speaker, or a wireless communications output to an external device that will generate a visual or auditory alarm.

Figure 3:
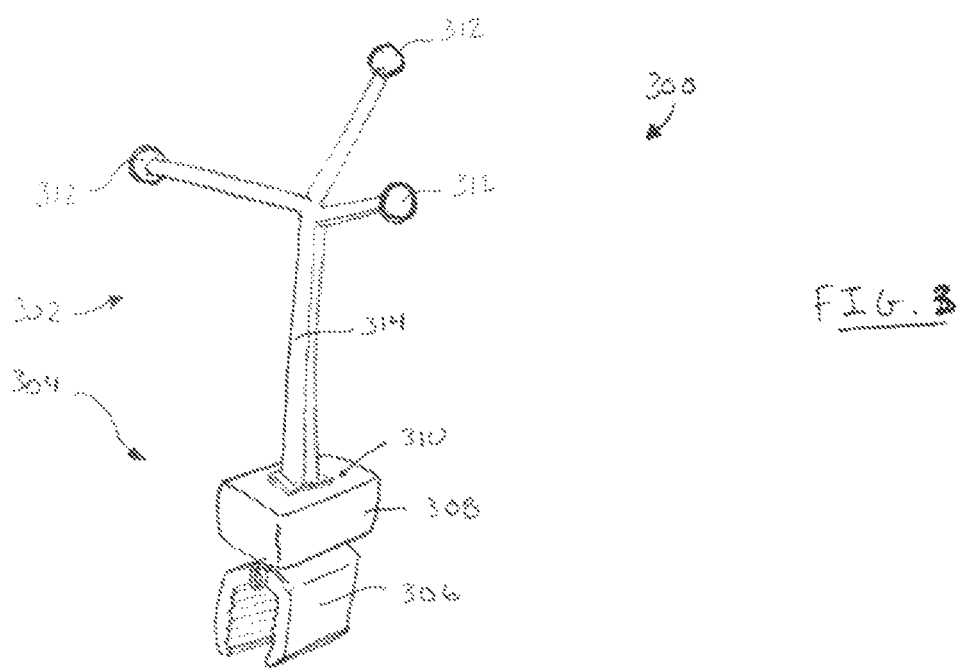
FIG. 3 shows a perspective view of one example embodiment of a multi-part patient reference device.

Reference is now made to FIG. 3, which shows a perspective view of one example embodiment of a multi-part patient reference device 300. The device 300 includes an optically-trackable array 302 and an attachment base 304. In this embodiment, the attachment base 304 includes a clamp mechanism 306 for securing the attachment base 304 to a bony structure, such as the spinous process, for example.

The attachment base 304 further includes a housing 308. The top of the housing 308 includes a quick-break attachment mechanism 310. The quick-break attachment mechanism 310 may include any coupling mechanism for attaching and securing the optically-trackable array 302 to the attachment base 304 in such a manner that it is secured in place in a pre-ordained orientation so that it may only be re-attached in exactly the same orientation and position. The quick-break attachment mechanism 310 may include a channel, slot, or other protrusion-groove structure to physically orient the optically-trackable array 302 to as to protrude outwards from the top of the housing 308. The channel, slot, etc., may be keyed to ensure proper orientation in a pre-determined position. The quick-break mechanism may include a magnetic connection to hold the optically-trackable array 302 in position on the attachment base 304 unless at least a threshold level of force overcomes the quick-break connection. The magnetic connection, which may be implemented as one or more permanent magnets in either side of the quick-break attachment mechanism 310, ensures a coupling force acts on the attachment base 304 and optically-trackable array 302 holding them in alignment and in connection. The level of force exerted by the quick-break attachment mechanism 310 is to be sufficient to ensure the optically-trackable array 302 is not too easily detached, such as by gravitational forces or minimal impact forces, but not so solidly attached that it will not detach in the case of an impact force that could risk dislodging the attachment base 304 from patient anatomy. That is the detachment force capable of overcoming the quick-break mechanism should be substantially lower than the force capable of dislodging the clamp mechanism 306 (or other attachment mechanism in other embodiments) from the patient anatomy.

The optically-trackable array 302 includes a geometric arrangement of fiducials 312 mounted on a stem 314 or longitudinally-extending arm that protrudes away from the attachment base 304. Other arrangements of fiducial 312, whether on a frame structure or on another substrate, may be used in other embodiments. The stem 314 functions to position the fiducials 312 spaced apart from the anatomy to make them more consistently and easily visible to tracking devices, e.g. cameras, of the navigation system during the surgical operation. In the case of a spinal surgery, particularly if there is more than one patient reference device being used in an operation (e.g. each attached to different vertebrae), the horizontally-compact vertically-oriented structure of the patient reference device 300 improves its usefulness in the surgical suite and reduces the likelihood of it being accidentally bumped because it obscures an area of interest. In this regard, it will be noted that the example patient reference device 300 is vertically aligned, such that the clamp mechanism 306, housing 308, and optically-trackable array 302 are all generally aligned along a common vertical axis.

Figure 4:
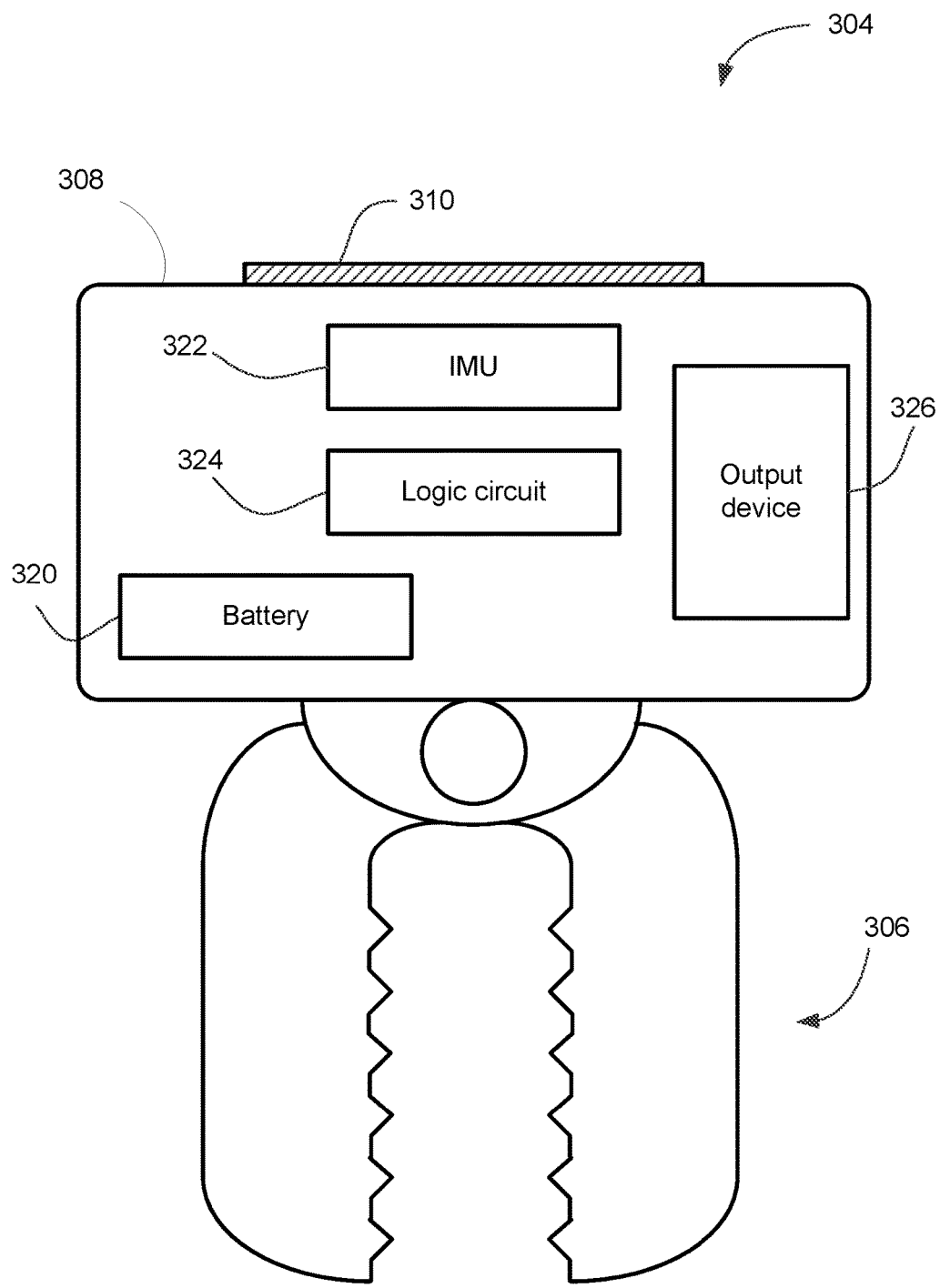
FIG. 4 shows, diagrammatically, one example embodiment of the attachment base.

Reference is now made to FIG. 4, which shows, diagrammatically one example embodiment of the attachment base 304. In this example embodiment, the attachment base 304 has a housing 308 that includes within it a battery 320, an IMU 322, a logic circuit 324 and an output device 326.

The IMU 322 generates signals, i.e. a motion signal, indicative of measured inertial forces on the attachment base 304. Together, the logic circuit 324 and the IMU 322 detect whether the attachment base 304 experiences more than a threshold change in position (rotation) or more than a threshold change in inertial acceleration forces (including gravitational forces, which could indicate positional change or rotation). The measured forces of the IMU 322 result in signals that may be comparted with a threshold by the logic circuit 324 and more than a threshold change in the IMU 322 measurements may trigger generation of an alarm signal that causes the output device 326 to output an alarm. Output of the alarm signal may be referred to as an alarm condition for the patient reference device. It will be appreciated that in some embodiments the IMU 322 and the logic circuit 324 may be considered an integral unit and may be implemented as a single integrated circuit component. The setting of a suitable threshold for determining that a detectable change has occurred may be implementation specific and may be altered to suit a particular sensitivity. The threshold level may be related to the relative positional change that such a movement would cause in the position, orientation, etc. of the trackable optical array, and may be set based on it causing more than a particular change in the position of the array, such as 0.5%, 1%, 3%, etc., or may be based on it causing an overall movement of more than a threshold distance by a point on the array, such as 1 mm, 2 mm, 5 mm, etc.

The output device 326 may include one or more LEDs or other such light output devices for signaling the alarm. In one example implementation, when the IMU 322 reaches a steady state, i.e. holds a stationary position, for at least a minimum time (e.g. 20-60 seconds, a few minutes, or longer), a green LED may be illuminated indicating that the attachment base 30 is in a stable stationary position. Upon detecting more than a threshold amount of movement, the IMU 322 and logic circuit 324 may cause illumination of the green LED to cease and may cause illumination of a red LED to indicate that the attachment base 304 has moved. To ensure the "moved" condition is not missed, in some other embodiments, the attachment base 304 may include an input device, such a button, switch, touch sensitive area, or other input mechanism (not illustrated) for receiving a reset command so that the attachment base 304 continues to display a "moved" red LED condition until it is manually reset.

In some embodiments, the output device 326 may include a speaker or other audio output mechanism for emitting an alarm sound in response to the alarm signal from the IMU 322 and logic circuit 324. The alarm sound may be a constant tone or series of tones, intermittent chirping, or any other audible alarm that will alert personnel in the operating room to the fact the attachment base 304 has moved.

In some embodiments, the attachment base 304 may include both the audible alarm and the visible alarm.

In yet other embodiments, the output device 326 includes a wireless communication system for transmitting the alarm signal to a remote device, which then outputs an alarm. For example, the wireless communication system may include a WiFi chip, a Bluetooth™ chip, a Near-Field Communications ("NFC") chip, or any other short-range RF wireless system for establishing a communications channel with another device. In another example, the wireless communication may be by RFID, whether active or passive, in which the navigation system polls one or more patient reference devices for information on the status of the device, i.e. whether an alarm state is active. If the output device 326 includes wireless communication capability, then any applicable "reset" command may be sent to the attachment base 304 over the communications channel from the remote device to which the wireless system is connected in order to cancel or reset the alarm condition.

Although the present example embodiment shows the attachment mechanism to be the clamp mechanism 306, other mechanisms for securing the attachment base 304 to patient anatomy may be used in other implementations. The clamp mechanism 306 may be useful in the case of spinal surgeries since the jaws of the clamp mechanism 306 may grip the protruding spinous process of a vertebrae. Nevertheless, in some cases adhesive, bone screws, or other attachment mechanisms may be considered advantageous in place of a physical clamp.

Figure 5:
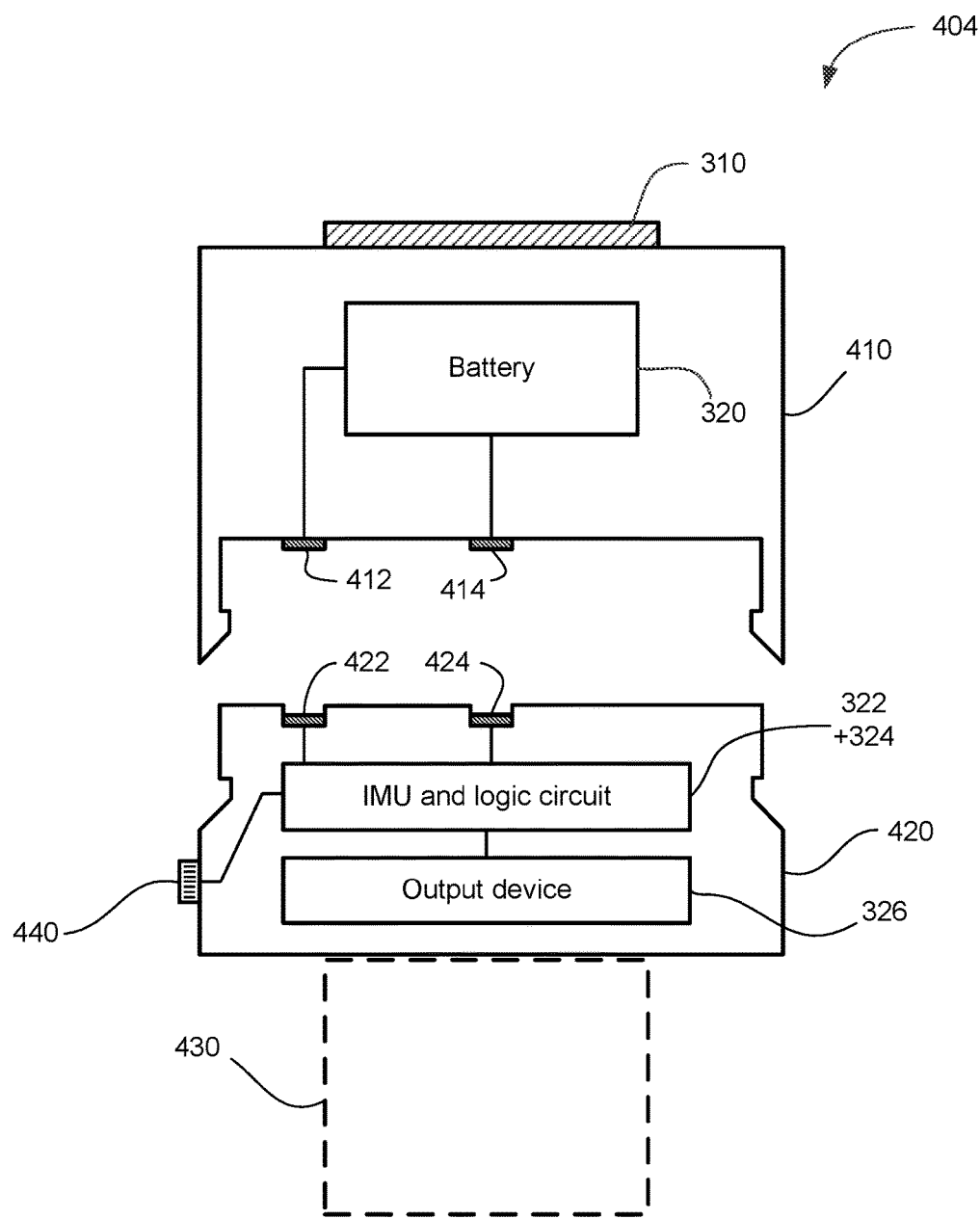
FIG. 5 shows another example embodiment of an attachment base.

Reference is now made to FIG. 5, which shows another example embodiment of an attachment base 404 for a patient reference device. In this example embodiment, the attachment base 404 is a two-part device that includes a sensor base 420 and a detachable battery housing 410. The battery housing 410 is designed to securely attach to the top of the sensor base 420. The top of the battery housing 410 includes one side of the quick-break attachment mechanism 310 for connecting the optically-trackable array. The underside of the battery housing 410 may feature contacts 412, 414 that are electrically connected to respective terminals of the battery 320 within the battery housing 410.

The sensor base 420 includes the IMU 322, the logic circuit 324 and the output device 326. It features an attachment mechanism 430 for securing the attachment base 404 to patient anatomy. The attachment mechanism 430 is illustrated generally and may include various attachments including mechanical clamps, pins, adhesive or other suitable attachment means.

The sensor base 420 includes an external casing with a top side that features contact pads 422 and 424 for electrically connecting to contacts 412 and 414, respectively. One or both of the contact pads 422, 424 or contacts 412, 414 may include a mechanical biasing, e.g. spring loading, to ensure solid contact when connected. The casings of the sensor base 420 and battery housing 410 feature a coupling mechanism that ensures the casings are securely attached in a fixed alignment and position relative to each other. In the present illustration, the coupling mechanism is depicted as a snap-fit mechanism but other attachment mechanisms may be used for other implementations.

One advantage of a two-part attachment base 404 is that the battery in the detachable battery housing 410 is separable from the sensor base 420. The sensor base 402 may contain relatively costly components, but the battery may be largely disposable. The sensor base 402 may be sterilized for re-use in subsequent surgical operations, whereas the detachable battery housing 410 may be disposed after use, since the battery may not be easily sterilized in some cases.

This example embodiment also shows the sensor base 420 including a reset input device 440, which in some examples may include a button or other manually-activated input mechanism. The reset input device 440 functions to send a signal to the IMU 322 and logic circuit 324 that causes them to start the operation of determining whether the attachment base 404 has moved more than a threshold amount based on the current inertial measurements. That is, the reset input device 440, when activated, signals that the attachment base 404 is in a stationary state and that any subsequent movement beyond the threshold level should cause an alarm. If any alarm is currently being output, then a signal from the reset input device 440 causes the alarm to cease until the IMU 322 and logic circuit 324 detect another indication of movement beyond the threshold level.

Figure 6:
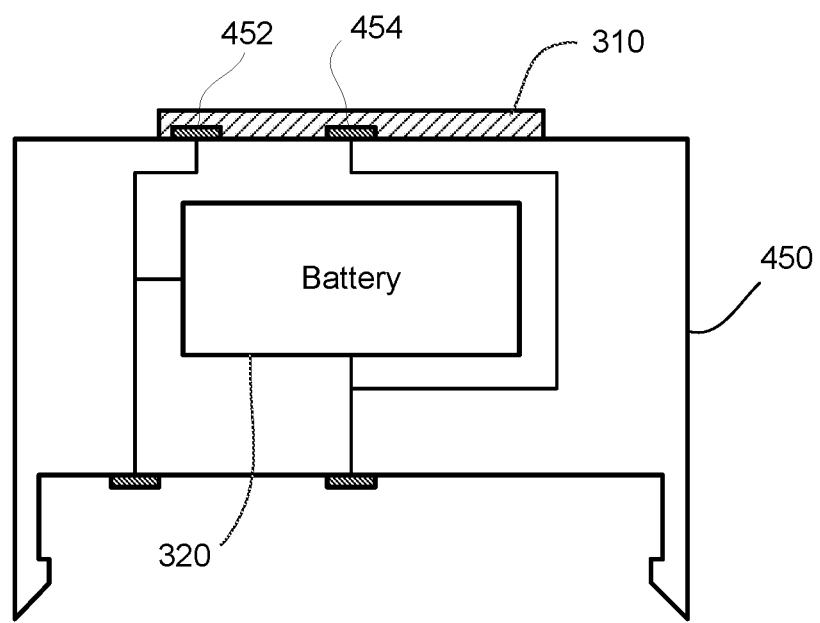
FIG. 6 shows an example of a battery housing.

Another embodiment of an example battery housing 450 is shown in FIG. 6. In this embodiment, the battery housing 450 includes additional battery contacts 452, 454 on the top of its casing to enable electrical DC power connection to the optically-trackable array. The additional battery contacts 452, 454 may be implemented as a part of the quick-break attachment mechanism 310 in some embodiments. Battery power may be used by the optically-trackable array in some implementations to power active fiducials, e.g. infrared LED-based fiducials, that emit energy as part of their function in assisting the navigation system to uniquely identify and track the optically-trackable array. In some cases, the active fiducials may include fiducials that emit light at different wavelengths in order to be distinguishable to the navigation system. The fiducials may be configured, internally or based on circuit elements in the optically-trackable array, to transmit light using a defined pattern or pulse frequency to further enable the navigation system to uniquely identify each fiducial. In yet other cases, the optically-trackable array may include logic circuitry or other computing elements to enable control of the active fiducials so as to receive optical communications from the navigation system and/or to transmit communications to the navigation system. Example communications may be receiving, possibly addressed, instructions regarding pulse patterns to use, or transmitting status information, such as battery level information.

In yet another embodiment, an example attachment base, in one or two parts, may contain the IMU, a battery and a wireless communication system. The attachment base may be configured to send IMU data to a navigation system regularly. The navigation system determines whether the IMU data indicates movement or not, and the navigation system outputs any alarms required as a result of detected movement of the attachment base.

Figure 7:
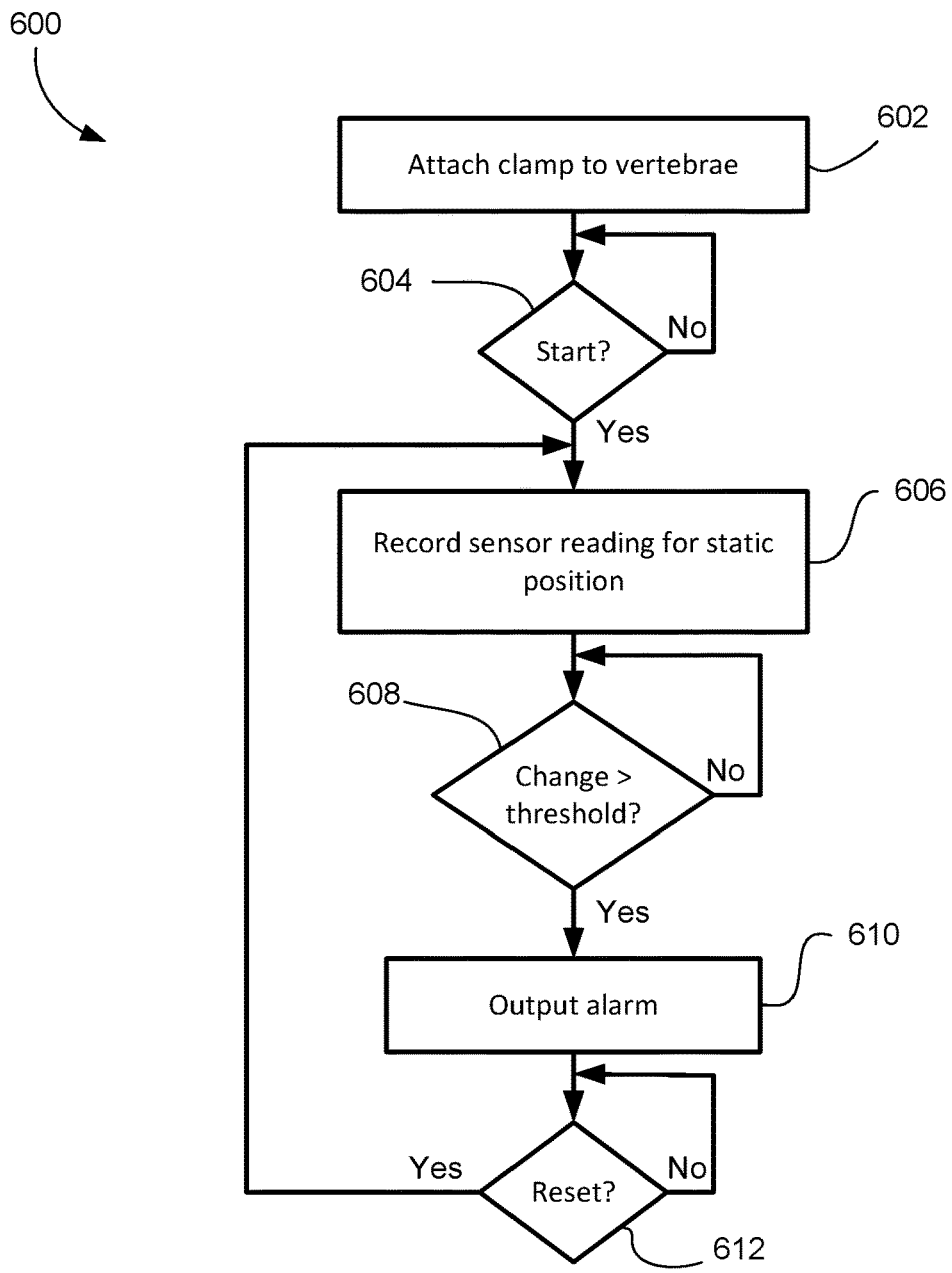
FIG. 7 shows, in flowchart form, one example method for tracking patient anatomy during a surgical operation.

Reference is now made to FIG. 7, which shows, in simplified flowchart form, one example method 600 for tracking patient anatomy during a surgical operation. The method 600 is carried out using a patient reference device, such as the example patient reference device 300 (FIG. 3) described above. In the operating room and in the course of surgery, the patient reference device 300 may be used to track patient anatomy. The patient anatomy may include anatomy that is intended to remain stationary during the operation, such as a hip, cranium, portion of the spine, etc., depending on the nature of the operation. In the present example, the patient reference device is to be attached to a vertebrae and, in particular, to the spinous process of a vertebrae. Accordingly, in operation 602 the patient reference device is clamped to a vertebrae.

In this example, the patient reference device is capable of receiving an input to trigger it to begin monitoring for movement. That is, it does not begin attempting to detect movement until instructed. That instruction or signal may be supplied via an input device, such a button or the like, that is actuated by personnel after the device is secured in place on the patient's anatomy. In some embodiments, that instruction may be communicated to the device wirelessly, where the device is equipped with a wireless communication system and capable of receiving such an instruction via RF or infrared communications, for example. In yet another embodiment, the instruction may be implemented simply as the supply of power; that is, attachment of the battery housing to the sensor base is the trigger for the sensor base to begin detecting movement. As shown in FIG. 7, the method 600 includes determining whether to start monitoring for movement in operation 604.

On determining that it is to start monitoring (by way of explicit instruction or command, or by way of implicit instruction, such as through supply of battery power), the device may then, in some embodiments, record current measurements from the IMU in operation 606, for comparison against future measurements. As indicated by operation 608 the device assesses whether there has been a change greater than a threshold level. In some embodiments, the recordal of starting measurements is not performed, as the IMU and logic circuitry simply attempt to detect a pseudo-instantaneous change in measurements that exceeds the threshold level. On the other hand in some embodiments the original measurements may be retained in order to detect relatively slow movements that, in time, result in more than a threshold change in position or orientation of the device.

If the device determines in operation 608 that the attachment base has undergone more than a threshold change in position or orientation, based on a more than threshold level change in the measurements of the IMU, then in operation 610 it outputs an alarm. As described above, the alarm may include a visual alarm, e.g. solid or flashing LED(s), an auditory alarm, e.g. speaker emitting tone or chirp, or a wireless communication to a remote device that signals the alarm. The alarm may include multiple types of alarms in combination in some cases.

In operation 612, the device determines whether the alarm has been cancelled and the device reset to a stationary position. Once that occurs, the process returns to operation 606 to monitor for movement.

In some cases, operation 612 may only involve stopping the alarm, and the process may return to operation 604 to await a further input command to re-start monitoring for movement. These commands may be input using the same input device or separate input devices. For example, a reset button may be pressed once to cancel the alarm output, but not restart the monitoring operation. After the device is repositioned and stationary, the reset button may be pressed again to trigger restarting of the monitoring operation, e.g. to progress from operation 604 to 606.

Certain adaptations and modifications of the described embodiments can be made. Therefore, the above discussed embodiments are considered to be illustrative and not restrictive.

What is claimed is:

1. A patient reference device for tracking anatomical location of a patient by an optical navigation system during a surgical procedure, the patient reference device comprising:
   an attachment base having an attachment mechanism to secure the attachment base to an anatomical feature of the patient;
   an optically-trackable array including a plurality of fiducials in a fixed geometric pattern to be detected by the optical navigation system and having a longitudinally-extending arm to space apart the fixed geometric pattern from the anatomical feature, the arm including a connector to be detachably secured to the attachment base;
   an inertial measurement unit in the attachment base to detect a change in position of the attachment base and to output a motion signal representing the change in position and its magnitude;
   a logic circuit to receive the motion signal and to compare it to a threshold level and, if the motion signal exceeds the threshold level, to generate an alarm signal; and
   an output device to output an alarm in response to the alarm signal.

2. The patient reference device claimed in claim 1, wherein the connector is a quick-break attachment mechanism.

3. The patient reference device claimed in claim 2, wherein the quick-break attachment mechanism includes at least one magnet of a first polarity, and wherein the attachment base includes at least one corresponding magnet of an opposite polarity.

4. The patient reference device claimed in claim 1, wherein the attachment base includes a housing containing a battery, the inertial measurement unit, the logic circuit and the output device.

5. The patient reference device claimed in claim 1, wherein the attachment base includes a sensor base containing the inertial measurement unit, the logic circuit and the output device and a detachable battery housing containing a battery to power the sensor base.

6. The patient reference device claimed in claim 5, wherein a top of the sensor base includes electrical contact pads, and wherein a bottom of the battery housing includes electrical contacts connected to respective terminals of the battery, and wherein the electrical contacts make electrical connections with respective contact pads when the battery housing is attached to the sensor base.

7. The patient reference device claimed in claim 1, wherein the attachment mechanism comprises a clamp to secure the attachment base to the anatomical feature.

8. The patient reference device claimed in claim 1, further comprising a reset mechanism for generating a signal to the logic circuit to reset an alarm condition.

9. The patient reference device claimed in claim 1, wherein the output device includes at least one of a light emitting diode or a speaker.

10. The patient reference device claimed in claim 1, wherein the attachment base, attachment mechanism, and optically trackable array are arranged along a common axis to project away from the anatomical feature.

11. The patient reference device claimed in claim 1, wherein the output device comprises a wireless communication system to connect to an external device, and wherein the alarm comprises a communication to the external device, and the external device, in response thereto, outputs a visual or auditory alarm event.

12. The patient reference device claimed in claim 1, further comprising an input device to generate a signal to cause the logic circuit to begin comparing the motion signal to the threshold level.

13. The patient reference device claimed in claim 12, wherein the input device comprises a button.

14. The patient reference device claimed in claim 12, wherein, if the patient reference device is in an alarm condition, then actuation of the input device is to cancel the alarm condition and if the device is not in the alarm condition, then actuation of the input device is to cause the logic circuit to begin comparing the motion signal to the threshold level.

15. The patient reference device claimed in claim 1, wherein the attachment base includes a battery, wherein the connector includes an electrical connection to supply battery power, and wherein the plurality of fiducials comprises at least one active fiducial to be powered by the battery power.

16. A method of tracking patient anatomy during a surgical operation using an optical navigation system and a patient reference device, the patient reference device being attached to an anatomical feature of the patient, the patient reference device including an attachment base having an attachment mechanism to secure the attachment base to the anatomical feature and a optically-trackable array including a plurality of fiducials in a fixed geometric pattern to be detected by the optical navigation system and having a longitudinally-extending arm to space apart the fixed geometric pattern from the anatomical feature, the arm including a connector to be detachably secured to the attachment base, the method comprising:

determining, based on comparing a threshold level to a motion signal from an inertial measurement unit within the attachment base, that the attachment base has changed position, wherein the motion signal represents the change in position and its magnitude;

based on determining that the attachment base has changed position, generating an alarm signal; and outputting, via an output device in the attachment base, an alarm in response to the alarm signal.

17. The method claimed in claim 16, further comprising receiving a reset signal, in response to the reset signal cancelling the alarm and the alarm signal, and repeating the determining.

18. The method claimed in claim 16, wherein outputting comprises illuminating a light emitting diode in the attachment base.

19. The method claimed in claim 16, wherein outputting comprises transmitting a short-range communication signal to an external device that outputs a visual or auditory alarm.

20. The method claimed in claim 16, further comprising first attaching the attachment base to the anatomical feature, securing the optically-trackable array to the attachment base once attached, and activating the inertial measurement unit.

\* \* \* \* \*